United States Patent [19]

Minekane

[11] Patent Number: 4,798,703

[45] Date of Patent: Jan. 17, 1989

[54] PHOTOMETRIC APPARATUS IN AUTOMATIC CHEMICAL ANALYZER

[75] Inventor: Tomiharu Minekane, Ootawara, Japan

[73] Assignee: Kabushiki Kaisha Toshiba, Kawasaki, Japan

[21] Appl. No.: 805,617

[22] Filed: Dec. 6, 1985

[30] Foreign Application Priority Data

Dec. 7, 1984 [JP] Japan ............................ 59-257406

[51] Int. Cl.$^4$ .......................................... G01N 35/04
[52] U.S. Cl. ........................................ 422/65; 422/67
[58] Field of Search .................... 422/63–67; 436/49

[56] References Cited

U.S. PATENT DOCUMENTS

| | | | |
|---|---|---|---|
| 3,897,216 | 7/1975 | Jones | 422/65 |
| 3,907,503 | 9/1975 | Betts et al. | 422/67 |
| 3,951,605 | 4/1976 | Natelson | 422/67 |
| 4,059,405 | 11/1977 | Sodrickson et al. | 422/67 |
| 4,113,436 | 9/1978 | Werder et al. | 422/65 |
| 4,158,545 | 6/1979 | Yamashita et al. | 422/67 |
| 4,265,855 | 5/1981 | Mandle et al. | 422/65 |
| 4,271,123 | 6/1981 | Curry et al. | 436/49 |
| 4,363,245 | 12/1982 | Schmid | 422/65 |
| 4,429,585 | 2/1984 | Beyer et al. | 422/67 |
| 4,536,369 | 8/1985 | Sakurada et al. | 436/47 |
| 4,549,809 | 10/1985 | Minekane et al. | 422/65 |
| 4,629,703 | 12/1986 | Uffenheimer | 422/63 |

Primary Examiner—Michael S. Marcus
Attorney, Agent, or Firm—Finnegan, Henderson, Farabow, Garrett, & Dunner

[57] ABSTRACT

A photometric apparatus for an automatic chemical analyzer is disclosed, which comprises a cell assembly, a photometric section, a drive unit, an edge detecting circuit, a signal generator and a control circuit. The cell assembly has cells for accommodating samples and arranged in a predetermined manner. The photometric section forms a light path for measurement and provides a detection signal obtained from the light path. The cell assembly and light path are moved relatively at a predetermined speed by the drive unit. With this movement, the cells are successively brought to a position on the light path. The edge detecting circuit detects an optical edge of the cell assembly from the detection signal of the photometric section. The signal generator is sensitive to the edge detection by the edge detecting circuit and generates an enable signal when a predetermined portion of each cell is brought to the position on the light path. The control circuit provides the photometric signal from the photometric section for analysis in response to the enable signal.

14 Claims, 4 Drawing Sheets

S1 OR S2

S4

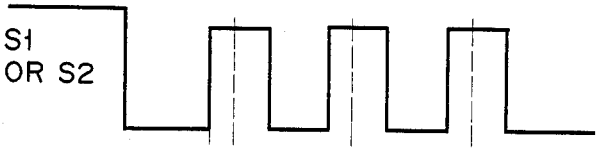
FIG. 5A S1 OR S2
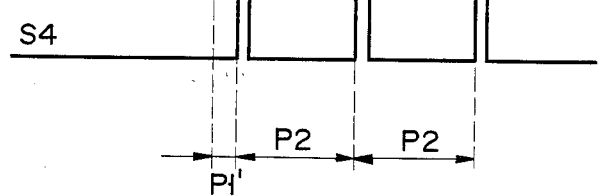
FIG. 5B S4

PHOTOMETRIC APPARATUS IN AUTOMATIC CHEMICAL ANALYZER

BACKGROUND OF THE INVENTION

This invention relates to a photometric apparatus for use in an automatic chemical analyzer and, more particularly, to a photometric apparatus which comprises a cell assembly with a plurality of containers, e.g., cells, arranged in a row and containing samples, the cells being caused to pass across a light path of a photometric section for direct measurement of the samples.

Most of the automatic chemical analyzers recently developed have a photometric apparatus of direct measurement type for determining the chemical properties of a sample contained in a cell by illuminating the cell.

In such a photometric apparatus, a measuring point of a cell containing a sample is designated by the signal generated when the cell passes across a light path in the optical system, and the signals obtained from the light transmitted through the measuring point of the cell are processed for light absorption analysis.

A prior art photometric apparatus will now be described with reference to FIG. 1.

The photometric apparatus shown in FIG. 1 comprises cell assembly 1, photometric section 2, position detecting section 3, drive unit 4 and control circuit 5.

Cell assembly 1 includes a plurality of cells 11A, 11B, ... which can contain samples and holder 12 holding the cells in a row at a predetermined interval. Holder 12 has windows 12a, 12b, ... through which cells 11A, 11B, ... are exposed. Windows 12a, 12b, ... form a light path in photometric section 2. Holder 12 has reflecting marks 13A, 13B, ... of aluminum foil, provided on the outer wall at predetermined positions beneath windows 12a, 12b, ... and in the light paths for cells 11A, 11B, ...

Photometric section 2 has light source 14, polychromator 15 and detector 16. Light source 14 and polychromator 15 face each other and set apart a predetermined distance, defining a light path. The light projected from source 14 advances along the light path and is applied to polychromator 15. Polychromator 15 has a diffraction grating and forms the spectrum of the light on detector 16. The spectrum consists of bands of negative first order light, 0th order light, first order light, second order light, and so on. Detector 16 detects these bands and generates signals representing these bands of light. The band of 0th order light is the component of the light, which has not been diffracted by polychromator 15. Generally, the bands of negative first order light and the band of first order light are used in photometrical analysis.

Position detector 3 includes light source 17 and light detector 18. Light source 17 and light detector 18 are disposed such that the detector receives the light projected from light source 17 and reflected by a reflecting mark among reflecting marks 13A, 13B, ... of cell assembly 1. Detector 18 generates a signal when it receives the light projected from light source 17 and reflected by one of reflecting marks 13A, 13B, ....

Drive unit 4 drives cell assembly 1 at a predetermined speed along a truck crossing the light path of photometric section 2. Windows 12a, 12b, ... are thus successively brought to a position on the light path. Control circuit 5 determines the measuring point of the optical system from the signal supplied from light detector 18, and supplies analyzing unit 6 with the photometric signal provided by detector 16. Analyzing unit 6 effects analysis by processing the photometric signal provided from control circuit 5.

In the above prior art photometric apparatus, reflecting marks 13A, 13B, ... are formed on the outer wall of the cell assembly at the measuring positions of cells 11A, 11B, .... These positions are determined according to the shape of the cells. When cells 11A, 11B, ... are cylindrical, the positions correspond to the centers of the cells. When the cells are rectangular, the positions correspond to the central portions of the cells. The photometric apparatus can determine the measuring positions by detecting reflecting marks 13A, 13B, ... by position detecting section 3.

In the automatic chemical analyzer, to obtain accurate results of analysis, the cells must be measured at the same position. Also, when each cell is repeatedly measured to identify the changes in reaction state of the sample, the cell must measured at the same position each time. Otherwise, accurate analysis can not be obtained.

An erroneous positioning of reflecting marks 13A, 13B, ..., reflecting marks 13A, 13B, ..., light source 17, or light detector 18, would disable detector 18 to accurately detect the measuring positions of the cells. An inaccurate detection of these positions makes an accurate analysis impossible even if no trouble is found in photometric section 2.

Further, a deviation of the parallelness of reflecting marks 13A, 13B, ... or contamination of thereof occurs over a long use of the apparatus. This also results in an error in measuring the positions of the cells, making an accurate analysis impossible.

Further, when position detecting section 3 has a trouble, it cannot accurately function, thus making an accurate analysis impossible even if no trouble is found in photometric section 2.

SUMMARY OF THE INVENTION

An object of the invention is to provide a photometric apparatus in an automatic chemical analyzer, which can make measurement of a cell accurately and with satisfactory reproducibility at all time so long as the photometric system, i.e., photometric section, is normal.

According to the invention, there is provided a photometric apparatus for an automatic chemical analyzer, which comprises a cell assembly having a plurality of cells containing samples, the cells being arranged in a predetermined manner, photometric section including light-projecter for projecting light and light-receiver for obtaining a signal including a photometric signal according to incident light, the light-projecter and light-receiver forming a light path therebetween for measurement, drive section for causing relative movement of the cell assembly and light path at a predetermined speed in the direction of arrangement of the cells of the cell assembly such that the cells are successively brought to the light path, edge detecting section for detecting an optical edge of the cell assembly from a signal obtained from the light-receiver of the photometric section, signal generating section for generating an enable signal in response to the edge detection by the edge detecting section and at a timing when a predetermined portion of each cell of the cell assembly appears at the light path, control section for providing the photometric signal obtained from the light-receiver of the photometric section for analysis in response to the enable signal from the signal generating section.

With the photometric apparatus according to the invention, direct measurement of cell can be made on the basis of a level change of photometric signal due to an optical edge of the cell assembly or a cell obtained when the cell assembly or cell passes across the light path of the photometric section.

BRIEF DESCRIPTION OF THE DRAWINGS

FIGS. 5A and 5B are views showing waveforms of a photometric signal and a sampling pulse in the photometric apparatus shown in FIG. 4.

DETAILED DESCRIPTION OF THE PREFERRED EMBODIMENTS

Figure 2:
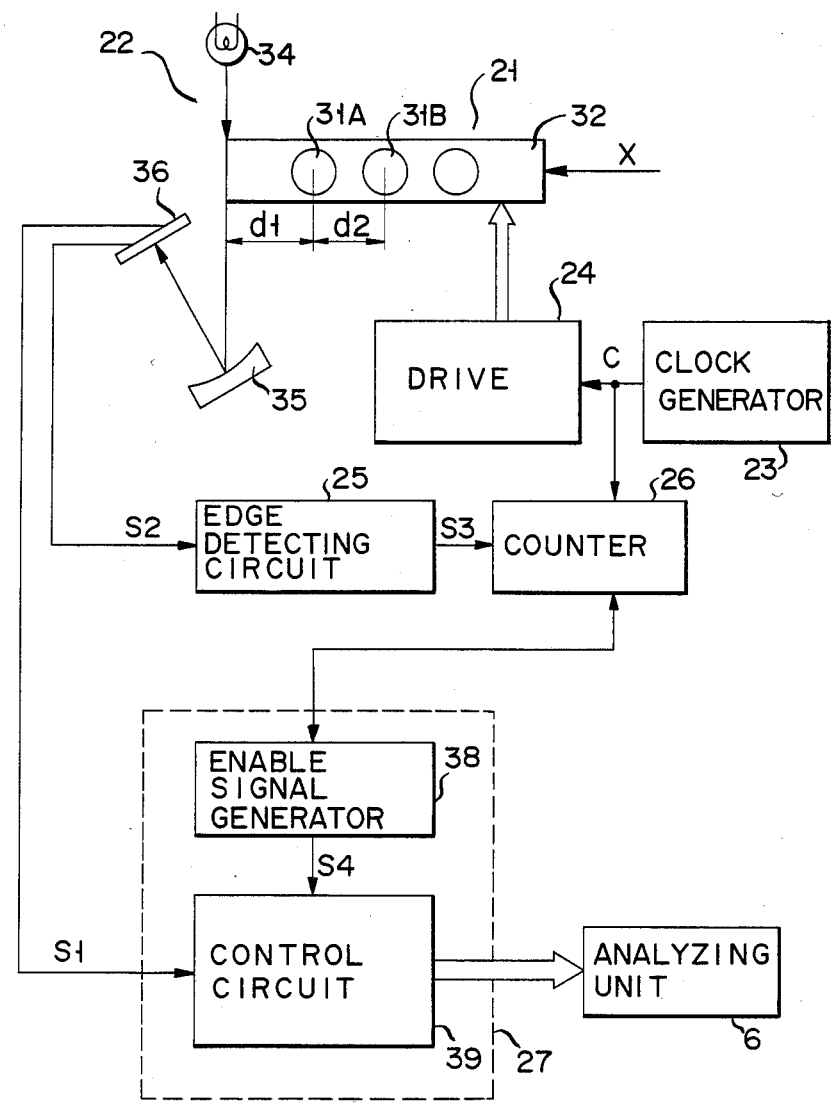
FIG. 2 is a schematic representation of a first embodiment of the photometric apparatus in an automatic chemical analyzer.

FIG. 2 shows a first embodiment of the photometric apparatus according to the invention.

The illustrated apparatus comprises cell assembly 21, photometric section 22, clock generator 23, drive unit 24, edge detecting circuit 25, counter 26 and control unit 27.

Cell assembly 21 includes a plurality of cells 31A, 31B, ... which can contain samples and holder 32 supporting cells 31A, 31B, ... in a row at a predetermined interval. Holder 12 has windows (not shown) formed at positions corresponding to respective cells 31A, 31B, ... Holder 32, unlike the case of FIG. 1, has no reflecting marks.

Figure 1:
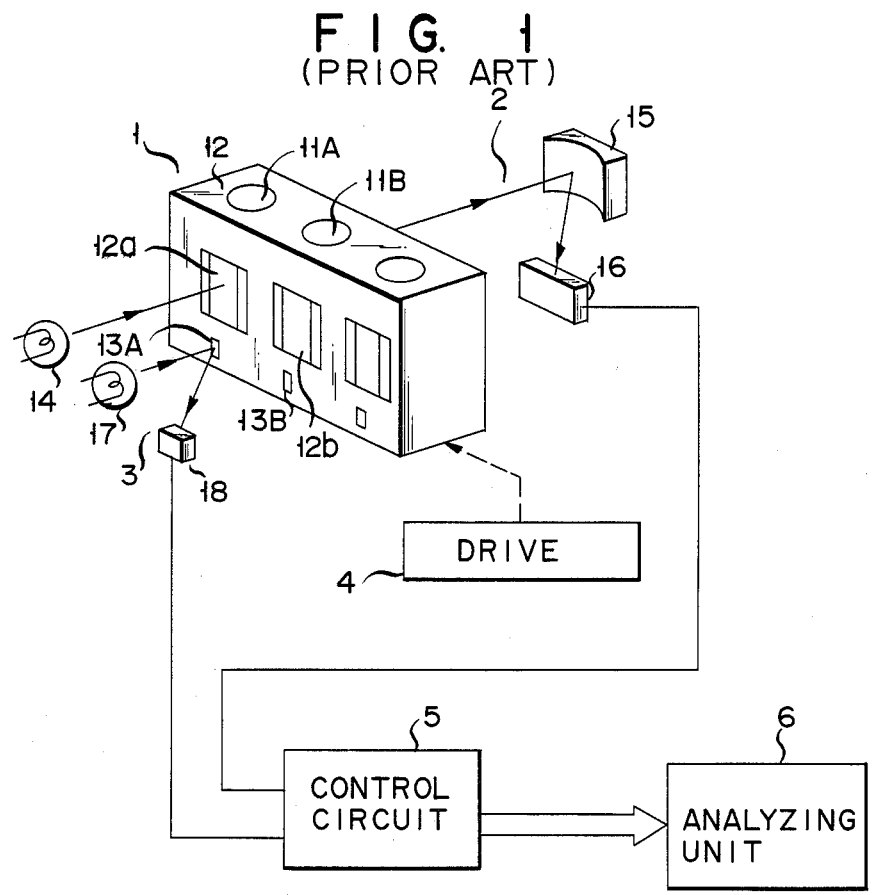
FIG. 1 is a schematic representation of a prior art photometric apparatus in an automatic chemical analyzer.

Photometric section 22 includes light source 34, polychromator 35 and detector 36, and it has substantially the same structure as photometric section 2 shown in FIG. 1. More specifically, light source 34 and polychromator 35 are spaced apart a predetermined distance and face each other to form a light path between them. Light projected from light source 34 along the light path noted above is incident on polychromator 35 which consists of a diffraction grating and produces a spectrum of the incident light. The spectrum formed by polychromator 36 on detector 36 is detected by detector 36. Detector 36 is a line sensor, e.g., a photodiode array. From the spectrum it generates photometric signal S1 corresponding to one of the bands forming the spectrum, e.g., the band of first order light, and also reference signal S2 corresponding to another band of the spectrum, which is unnecessary for photometrical analysis, e.g., the band of 0th order light.

Clock generator 23 generates a clock pulse train c at a fixed frequency.

Drive unit 24 drives cell assembly 21 at a predetermined speed along a (not shown) crossing the light path in photometric section 22, whereby windows for respective cells 31A, 1B, ... are successively brought to a position on the light path in photometric section 22. Drive unit 24 uses a pulse motor (not shown) as a drive source, and it moves cell assembly 21 in the direction shown by arrow X at a speed of 0.25 mm per cycle of clock pulse train c, provided from clock generator 23, for instance, in response to the clock pulse train.

Edge detecting circuit 25 detects a level change of reference signal S2 provided from detector 36 in photometric section 22 when the leading edge of cell assembly 21 enters the light path in response to reference signal S2 and produces detection pulse S3.

Counter 26 is reset and started by detection pulse S3 from edge detecting circuit 25 to count pulses from clock generator 23. When its count reaches a predetermined count, counter 26 produces a control signal and is reset by a signal from control unit 27.

Control section 27 includes enable signal generator 38 and control circuit 39, and it receives output signal S1 of photometric section 22 and transfers it to analyzing unit 6 in an interlocked relation to counter 26. Enable signal generator 38 generates enable signal S4 in response to the control signal provided from counter 26. It also provides a reset signal to counter 26 to reset the same. Control circuit 39, when receiving enable signal S4 from enable signal generator 38, transfers signal S1 from detector 36 of photometric section 22 to analyzing unit 6. More specifically, a predetermined period of time passed after the edge detection by edge detecting circuit 25 is counted by counter 26, and enable signal generator 38 and control circuit 39 are rendered operative at a predetermined timing. At this moment, signal S1 is provided for analysis in analyzing unit 6.

Figure 3A:
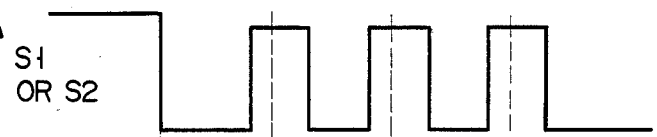
FIGS. 3A and 3B are views showing waveforms of a photometric signal and a sampling signal in the photometric apparatus shown in FIG. 2.
Figure 3B:
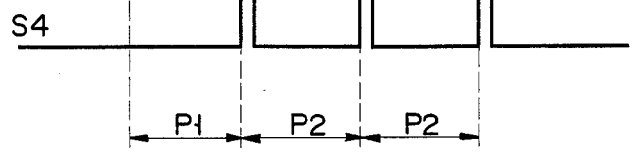

The operation of the above photometric apparatus will now be described. The waveform of signal S1 or signal S2 provided from detector 36 of photometric section 22 is shown in FIG. 3A, and the waveform of enable signal S4 provided from enable signal generator 38 of control section 27 is shown in FIG. 3B. Light is not transmitted through holder 32 of cell assembly 21 other than the windows.

Drive unit 24 drives cell assembly 21 in response to clock pulse train c provided from clock generator 23. That is, cell assembly 21 is moved in the direction of arrow X at a speed of 0.25 mm per pulse cycle period.

While cell assembly 21 is not inserted in photometric section 22, detector 36 is feeding signal S1 to control circuit 39 and signal S2 to edge detecting circuit 25.

In this state, counter 26 has not been started yet. Control section 27, therefore, does not designate measurement point, i.e., does not transfer signal S1 to analyzing unit 6.

When cell assembly 21 is brought to the light path between light source 34 and polychromator 35 in photometric section 22, the light path is blocked by cell assembly 21. As a result, both signals S1 and S2 provided from detector 36 fall to zero level, as shown in FIG. 3A. Edge detecting circuit 25 detects this level change of signals S1 and S2 to feed a detection pulse to counter 26. In response to this detection pulse, counter 26 starts to count clock pulse train c from clock generator 23.

Signals S1 and S2, as shown in FIG. 3A, have substantially a rectangular waveform. This represents the passage of the successive windows of cell assembly 21 across the light path with the movement of the cell assembly. In this embodiment, distance d1 from the leading edge of cell assembly 21 to the center of first cell 31A is set to 25 mm, center-to-center distance d2 between adjacent cells 31A and 31B is set to 15 mm, and the width of the windows is set to 10 mm. When pulse count P1 of counter 26 started in response to detection pulse S3 from edge detecting circuit 25 reaches 100, first cell 31A of cell assembly 21 is found on the light path of photometric section 22. At this time, the control signal is fed from counter 26 to enable signal generator 38 in control section 27, and enable signal S4 is fed from enable signal generator 38 to control circuit 39, as shown in FIG. 3B. Photometric signal S1 at this time corresponds to light transmitted through the center of first cell 31A. In response to this enable signal S4 control circuit 39 is rendered operative to transfer signal S1 to analyzing unit 6. Thus, a spectrum corresponding to the accurate center of cell is provided for analysis. Counter 26 is reset by a signal which is provided form enable signal 38 simultaneously with the generation of enable signal S4.

Since cell assembly 21 is fed at a constant speed in the direction of arrow X, light form light source 34 is subsequently blocked by the wall portion of holder 32 between the windows for first and second cells 31A and 31B. Consequently, signals S1 and S2 again fall to zero level. With the appearance of the window for second cell 31B at the light path, signals S1 and S2 rise again.

Counter 26, having provided the control signal for generating the first enable signal, is reset and starts counting of clock c again. When count P2 of counter 26 reaches 60, the center of second cell 31B is found on the light path of photometric section 22. At this instant, counter 26 feeds control signal to enable signal generator 38, which thus feeds a second enable signal S4 to control circuit 14. The second measuring point thus is designated. Photometric signal provided at this time corresponds to the center of second cell 31B. This signal S1 is fed to analyzing unit 6. At the time of generation of enable signal S4 counter 26 is reset again.

Measurement with respect to the third and following cells is performed in the manner as described above. Thus, measurement of the center of successive cells 31A, 31B, . . . is effected accurately and with satisfactory reproducibility.

Photometric signal S1 corresponding to the center of each of cells 31A, 31B, . . . obtained in this way is fed to successively fed to analyzing unit 6 for clinical analysis.

Figure 4:
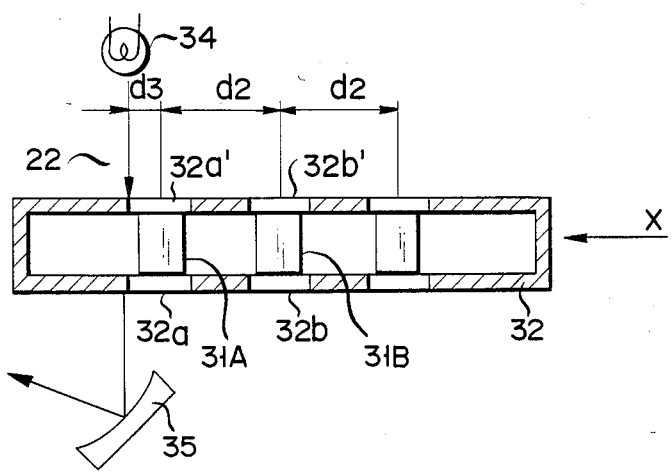
FIG. 4 is a view showing a portion of a second embodiment of the photometric apparatus according to the invention.

A second embodiment of the photometric apparatus according to the invention will now be described with reference to FIGS. 4, 5A and 5B. This embodiment is different from the preceding embodiment shown in FIG. 2 in that edge detecting circuit 25 (which is not shown in FIG. 4) detects a level change of reference signal S2 when the first (i.e., inner) edge of first window 32a (32a') among windows 32a (32a'), 32b (32b'), . . . corresponding to respective cells 31A, 31B of cell assembly 21 appears on the light path in the photometric section. In this case, if distance d3 from the first edge noted above to the center of first cell 31A is 5 mm, count P1 of counter 26, with which the control signal for generating first enable signal S4 is fed to enable signal generator 38, is 20. Second and following enable signals S4 are generated in the same manner as described in connection with the photometric apparatus shown in FIG. 2. This embodiment particularly permits accurate measurement of the center of an angular cell.

The above embodiments of the invention are by no means limitative, and various changes and modifications are possible without departing from the scope and spirit of the invention.

For example, the measuring position of each cell may be determined through counting of a predetermined period of time with respect to the instant of detection of the first edge of each of windows 32a (32a'), 32b (32b'), . . . of holder 32 of cell assembly 21.

Further, instead of causing the driving of cell assembly 21 and counting of time by operating drive unit 24 and counter 26 according to the output of clock generator 23, it is possible to employ an encoder, which generates a pulse train consisting of pulses each provided for a fixed amount of relative movement of the cell assembly and light path of photometric section 22.

What is claimed is:

1. A photometric apparatus in an automatic chemical analyzer, comprising:

photometric means including light-projecting means for projecting light and light-receiving means for obtaining a signal including a photometric signal from incident light projected by said light-projecting means, said light-projecting and light-receiving means forming a light path therebetween for measurement;

a cell assembly including a holder having an optical edge for obstructing said light path and a plurality of cells containing samples to be analyzed, said cells being spaced apart in said holder in a conveying direction and one of said cells being adjacent said optical edge, each of said cells having an analyzing portion located at a preselected position therein, said analyzing portions of adjacent cells being separated by a first predetermined distance and said analyzing portion of said cell adjacent said optical edge being separated from said optical edge by a second predetermined distance;

drive means for causing relative movement between said cell assembly and said light path at a predetermined speed in said conveying direction for positioning said cells successively in said light path between said light-projecting means and said light-receiving means;

edge detecting means responsive to said light-receiving means for detecting the passage of said optical edge of said holder through said light path;

signal generating means responsive to said drive means and to the detection of said optical edge of said holder by said edge detecting means for generating an enable signal for measurement of said cells at said analyzing portions, said signal generating means including means for generating said enable signal upon detection of said optical edge and at succeeding intervals determined by a relationship between at least one of the predetermined distances between said optical edge and said adjacent portion of an adjacent cell and respective analyzing portions of adjacent cells, and said predetermined speed of movement of said cell assembly;

means for analyzing said photometric signal obtained by said light-receiving means from incident light projected by said light-projecting means and passing through said cells; and control means responsive to said enable signal from said signal generating means for transmitting said photometric signal obtained by said light-receiving means to said analyzing means for photometric analysis of said cells at times when said analyzing portions of said cells appear in said light path.

2. The apparatus according to claim 1, wherein said edge detecting means effects edge detection through detection of a sudden level change of the signal obtained from said light-receiving means of said photometric means.

3. The apparatus according to claim 4, wherein said edge detecting means includes differentiating means for detecting a sudden level change of the signal obtained from said light-receiving means of said photometric means.

4. The apparatus according to claim 1, wherein said edge detecting means effects edge detection from the photometric signal obtained from said lightreceiving means of said photometric means.

5. The apparatus according to claim 1, wherein said photometric means includes polychromator means provided in said light path, said light-projecting means of said photometric means projects light containing a plurality of different wavelength components, and said light-receiving means of said photometric means is a line sensor for detecting a spectrum produced from said polychromator means.

6. The apparatus according to claim 5, wherein said light-projecting means projects white light.

7. The apparatus according to claim 1, wherein said photometric means includes polychromator means provided in said light path, said light-projecting means of said photometric means projects light containing a plurality of different wavelength components, said light-receiving means of said photometric means is a line sensor for detecting a spectrum provided from said polychromator means, and said edge detecting means is responsible to a component of a detection signal provided from said line sensor that is not directly used for analysis.

8. The apparatus according to claim 7, wherein said edge detecting means responds to that component of the light which corresponds to the band of 0th order light.

9. The apparatus according to claim 7, wherein said edge detecting means responds to that component of the light which is not used in photometrical analysis.

10. The apparatus according to claim 1, wherein said signal generating means includes counting means for calculating the elapsed time between detection of the passage of said optical edge through said light path by said edge detecting means and the appearance of said analyzing portion of each of said cells in said light path as said holder moves through said light path.

11. The apparatus according to claim 1, wherein said signal generating means includes time-measuring means for measuring an elapsed time starting from the detection of said optical edge.

12. The apparatus according to claim 11, wherein said drive means includes a clock generator for generating clock pulses, and said time-measuring means includes a counter for counting said clock pulses.

13. A photometric apparatus in an automatic chemical analyzer, comprising:

photometric means including light-projecting means for projecting light and light-receiving means for obtaining a signal including a photometric signal from incident light projected by said light-projecting means, said light-projecting and light-receiving means forming a light path therebetween for measurement;

a cell assembly including a holder having an exterior leading edge for initiating obstruction of said light path and a plurality of cells containing samples to be analyzed, said cells being spaced apart in said holder in a conveying direction and one of said cells being adjacent said leading edge, each of said cells having an analyzing portion located at a preselected position therein, said analyzing portions of adjacent cells being separated by a first predetermined distance and said analyzing portion of said cell adjacent said leading edge being separated from said leading edge by a second predetermined distance;

drive for means causing relative movement between said cell assembly and said light path at a predetermined speed in said conveying direction for positioning said cells successively in said light path between said light-projecting means and said light-receiving means;

edge detecting means responsive to said light-receiving means for detecting the passage of said leading edge of said holder through said light path;

signal generating means responsive to said drive means and the detection of said optical edge of said holder by said edge detecting means for generating an enable signal at times when said analyzing portion of each of said cells appears at said light path, said signal generating means including counting means for calculating the elapsed time between detection of the passage of said leading edge through said light path by said edge detecting means and the appearance of said analyzing portions of each of said cells in said light path as said holder moves through said light path at said predetermined speed;

means for analyzing said photometric signal obtained by said light-receiving means from incident light projected by said light-projecting means and passing through said cells; and control means responsive to said enable signal from said signal generating means for transmitting said photometric signal obtained by said light-receiving means to said analyzing means for photometric analysis of said cells at times when said analyzing portions of said cells appear in said light path.

14. A photometric apparatus in an automatic chemical analyzer comprising:

photometric means including light-projecting means for projecting light and light-receiving means for obtaining a signal including a photometric signal from incident light projected by said light-projecting means, said light-projecting and light-receiving means forming a light path therebetween for measurement;

a cell assembly including a holder having a plurality of window means spaced apart in a conveying direction for permitting light to pass through selected portions of said holder, the leading edge of the leading one of said window means constituting an optical edge for initiating the passage of said light path blocked by said holder, said cell assembly further including a plurality of cells each positioned at one of said window means and containing a sample to be analyzed, said cells being spaced apart in said holder in said conveying direction and one of said cells being adjacent said optical edge, each of said cells having an analyzing portion located at a preselected position therein, said analyzing portions of adjacent cells being separated by a first predetermined distance and said analyzing portion of said cell adjacent said optical edge being separated from said optical edge by a second predetermined distance;

drive means for causing relative movement between said cell assembly and said light path at a predetermined speed in said conveying direction for positioning said cells successively in said light path between said light-projecting means and said light-receiving means;

edge detecting means responsive to said light-receiving means for detecting the passage of said optical edge of said holder through said light path;

signal generating means responsive to said drive means and to the detection of said optical edge of said holder by said edge detecting means for generating an enable signal at times when said analyzing portion of each of said cells appears at said light path, said signal generating means including counting means for calculating the elapsed time between detection of the passage of said optical edge through said light path by said edge detecting means and the appearance of each of said analyzing portions of each of said cells in said light path as said holder moves through said light path at said predetermined speed;

means for analyzing said photometric signal obtained by said light-receiving means for incident light projected by said light-projecting means and passing through said cells; and control means responsive to said enable signal of said signal generating means for transmitting said photometric signal obtained by said light-receiving means to said analyzing means for photometric analysis of said cells at times when said analyzing portions of said cells appear in said light path.

* * * * *